United States Patent
Jiang et al.

(10) Patent No.: US 11,434,270 B2
(45) Date of Patent: Sep. 6, 2022

(54) PROTEIN FOR NEUTRALIZING PROGRAMMED NECROCYTOSIS PROMOTION ANTIBODY, AND APPLICATION OF PROTEIN

(71) Applicant: SHANGHAI JW INFLINHIX CO., LTD., Shanghai (CN)

(72) Inventors: Shisong Jiang, Shanghai (CN); Wenshu Lu, Shanghai (CN)

(73) Assignee: SHANGHAI JW INFLINHIX CO., LTD., Shanghai (CN)

( * ) Notice: Subject to any disclaimer, the term of this patent is extended or adjusted under 35 U.S.C. 154(b) by 566 days.

(21) Appl. No.: 15/779,282

(22) PCT Filed: Nov. 25, 2016

(86) PCT No.: PCT/CN2016/107291
§ 371 (c)(1),
(2) Date: May 25, 2018

(87) PCT Pub. No.: WO2017/088821
PCT Pub. Date: Jun. 1, 2017

(65) Prior Publication Data
US 2019/0144517 A1    May 16, 2019

(30) Foreign Application Priority Data

Nov. 26, 2015    (CN) .......................... 201510844422.1

(51) Int. Cl.
| | | |
|---|---|---|
| *C07K 14/525* | (2006.01) | |
| *A61M 1/14* | (2006.01) | |
| *C07K 7/06* | (2006.01) | |
| *A61P 19/02* | (2006.01) | |
| *A61P 29/00* | (2006.01) | |
| *A61K 9/00* | (2006.01) | |
| *A61M 1/36* | (2006.01) | |
| *A61K 38/00* | (2006.01) | |

(52) U.S. Cl.
CPC .......... *C07K 14/525* (2013.01); *A61K 9/0019* (2013.01); *A61M 1/14* (2013.01); *A61M 1/3687* (2013.01); *A61P 19/02* (2018.01); *A61P 29/00* (2018.01); *C07K 7/06* (2013.01); *A61K 38/00* (2013.01)

(58) Field of Classification Search
CPC .... A61K 38/00; A61K 9/0019; C07K 14/525; C07K 7/06; C07K 7/08; A61P 19/02; A61P 29/00; A61M 1/14
See application file for complete search history.

(56) References Cited

U.S. PATENT DOCUMENTS

2004/0099596 A1* 5/2004 Naghavi ............... A61M 1/14
                                                      210/321.6

FOREIGN PATENT DOCUMENTS

| CN | 102776264 A | 11/2012 |
|---|---|---|
| CN | 106046144 A | 10/2016 |
| EP | 3 333 189 | 6/2018 |

OTHER PUBLICATIONS

Altreya, R., et al. Antibodies against tumor necrosis factor (TNF) induce T-cell apoptosis in patients with inflammatory bowel disease via TNF receptor 2 and intestinal CD14+ macrophages. Gastroenterology, 2011, 141:2026-2038.*
CN102776264, published Nov. 14, 2012, English translation of original document.*
Lu, W., et al. Evoloutionarily conserved primary TNF sequences relate to its primitive functionsin cell death induction. J. Cell. Sci., 2016, 129:108-120.*
Chan et al., "Signaling by the TNF receptor superfamily and T cell homeostasis" Immunity vol. 13, pp. 419-422, Oct. 2000.
Thoma et al., "Identification of a 60-kD tumor necrosis factor (TNF) receptor as the major signal transducing component in TNF responses", J. Exp. Med. vol. 172, pp. 1019-1023. Oct. 1990.
Idriss et al. "TNF α and the TNF receptor superfamily: structure-function relationship(s)" Microscopy Research and Technique 50, pp. 184-195, 2000.
Van Herreweghe et al., "Tumor necrosis factor-mediated cell death: to break or to burst, that's the question" Cellular and Molecular Life Sciences 67, pp. 1567-1579, 2010.
Kono et al, "How dying cells alert the immune system to danger" Nat Rev Immunol. 8, pp. 279-289, Apr. 2008.
Declercq et al., "RIP kinases at the crossroads of cell death and survival", Cell 138, pp. 229-232, Jul. 24, 2009.
Hitomi et al., "Identification of a molecular signaling network that regulates a cellular necrotic cell death pathway", Cell 135, pp. 1311-1323, Dec. 26, 2008.
Galluzzi et al., "Necroptosis: a specialized pathway of programmed necrosis", Cell 135, pp. 1161-1163, Dec. 26, 2008.
Vandenabeele et al., "Molecular mechanisms of necroptosis: an ordered cellular explosion", Nature Reviews Molecular Cell Biology 11, pp. 700-714, Oct. 2010.
Vanden Berghe et al., "Necroptosis, necrosis and secondary necrosis converge on similar cellular disintegration features", Cell Death and Differentiation 17, pp. 922-930, 2010.
Chan et al., "A role for tumor Necrosis factor receptor-2 and receptor-interacting protein in programmed necrosis and antiviral responses" J. Biol. Chem. vol. 278, No. 61, pp. 51613-51621, Dec. 19, 2003.
Feldmann, M., Translating molecular insights in autoimmunity into effective therapy. Annu. Rev. Immunol. 27, pp. 1-27, Nov. 13, 2008.

(Continued)

*Primary Examiner* — Prema M Mertz
(74) *Attorney, Agent, or Firm* — Hamre, Schumann, Mueller & Larson, P.C.

(57) ABSTRACT

Provided is polypeptide which derives from wild type TNF a and inhibits necrocytosis. The polypeptide contains 10-200 amino acid residues and a sequence QLVVPSE. Also provided is a pharmaceutical composition containing polypeptide. The polypeptide and the pharmaceutical composition containing the polypeptide are capable of inhibiting necrocytosis, thereby being used for treating inflammatory diseases.

6 Claims, 8 Drawing Sheets
Specification includes a Sequence Listing.

(56) References Cited

OTHER PUBLICATIONS

Scheinfeld, N., "A comprehensive review and evaluation of the side effects of the tumor necrosis factor α blockers etanercept, infliximab and adalimumab", Journal of Dermatological Treatment 15, pp. 280-294, 2004.

Gunther et al., "Apoptosis, necrosis and necroptosis: cell death regulation in the intestinal epithelium" Gut 62, pp. 1062-1071, 2013.

Rock et al., "The inflammatory response to cell death", Annu Rev Pathol. 3, pp. 99-126, 2008.

Linkermann et al., "Necroptosis", N Engl J Med. 370, pp. 455-465, Jan. 30, 2014.

International Search Report and Written Opinion; International Patent Application No. PCT/CN2016/107291, dated Mar. 1, 2017, with English translation of Search Report (15 pages).

Extended European Search Report issued in European Patent Application No. 16868044.5, dated Jul. 11, 2019, 8 pages.

Office Action issued in Japanese Application No. 2018-546736, dated Dec. 18, 2020, with English translation.

Steed, P.M. et al., "Inactivation of TNF signaling by rationally designed dominant-negative TNF variants ", Science, (2003), vol. 301, pp. 1895-1898.

Jones, E.Y. et al., "The structure of tumour necrosis factor—implications for biological function", J Cell Sci, 1990, No. Suppl. 13, pp. 11-18.

Ostade et al., "Localization of the active site of human tumour necrosis factor (hTNF) by mutational analysis", The EMBO Journal, Apr. 1991, 10(4), pp. 827-836.

Van Ostade, X. et al., "Human tumor necrosis factor mutants with preferential binding to and activity on either the R55 or R75 receptor", Eur J Biochem, (1994), vol. 220, pp. 771-779.

* cited by examiner

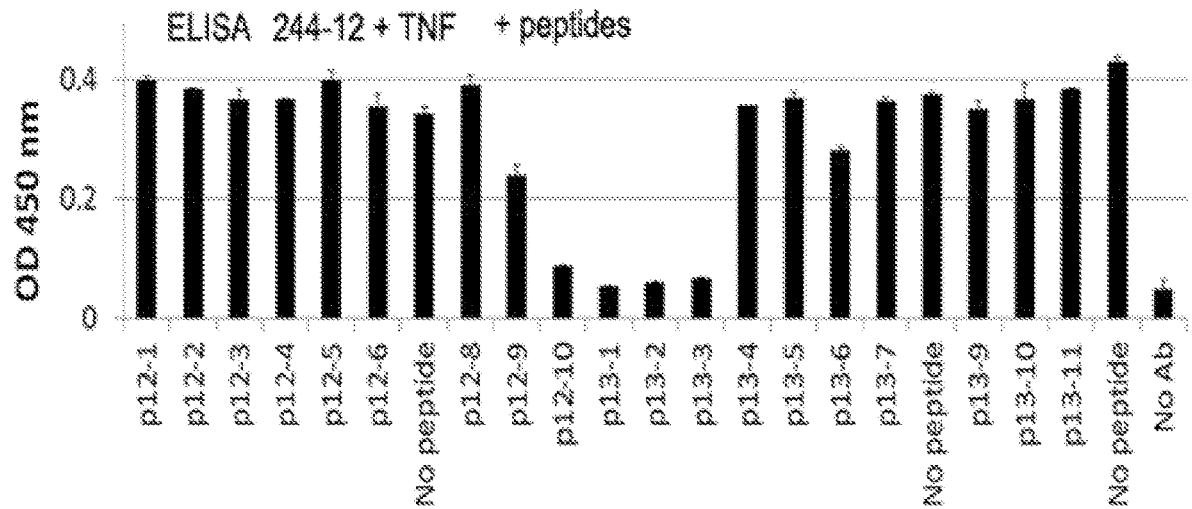

P12-
1. ALLANGVELR (SEQ ID NO: 12)
2. LLANGVELRD (SEQ ID NO: 13)
3. LANGVELRDN (SEQ ID NO: 14)
4. ANGVELRDNQ (SEQ ID NO: 15)
5. NGVELRDNQL (SEQ ID NO: 16)
6. GVELRDNQLV (SEQ ID NO: 17)
7. VELRDNQLVV (SEQ ID NO: 18)
8. ELRDNQLVVP (SEQ ID NO: 19)
9. LRDNQLVVPS (SEQ ID NO: 20)
10. RDNQLVVPSE (SEQ ID NO: 5)

P13-
1. DNQLVVPSEG (SEQ ID NO: 6)
2. NQLVVPSEGL (SEQ ID NO: 7)
3. QLVVPSEGLY (SEQ ID NO: 8)
4. LVVPSEGLYL (SEQ ID NO: 21)
5. VVPSEGLYLI (SEQ ID NO: 22)
6. VPSEGLYLIY (SEQ ID NO: 23)
7. PSEGLYLIYS (SEQ ID NO: 24)
8. SEGLYLIYSQ (SEQ ID NO: 25)
9. EGLYLIYSQV (SEQ ID NO: 26)
10. GLYLIYSQVL (SEQ ID NO: 27)
11. LYLIYSQVLF (SEQ ID NO: 28)

Fig.11

SEQUENCE LISTING

```
<160> NUMBER OF SEQ ID NOS: 28

<210> SEQ ID NO 1
<211> LENGTH: 233
<212> TYPE: PRT
<213> ORGANISM: Homo sapiens

<400> SEQUENCE: 1

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 2
<211> LENGTH: 157
<212> TYPE: PRT
<213> ORGANISM: Artificial sequence
<220> FEATURE:
```

<223> OTHER INFORMATION: Polypeptide

<400> SEQUENCE: 2

```
Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Phe His Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys
        115                 120                 125

Gly Asp Arg Leu Ser Ala Glu Ile Asn Arg Pro Asp Tyr Leu Asp Phe
    130                 135                 140

Ala Glu Ser Gly Gln Val Tyr Phe Gly Ile Ile Ala Leu
145                 150                 155
```

<210> SEQ ID NO 3
<211> LENGTH: 80
<212> TYPE: PRT
<213> ORGANISM: Artificial sequence
<220> FEATURE:
<223> OTHER INFORMATION: Polypeptide

<400> SEQUENCE: 3

```
Gln Leu Gln Trp Leu Asn Arg Arg Ala Asn Ala Leu Leu Ala Asn Gly
1               5                   10                  15

Val Glu Leu Arg Asp Asn Gln Leu Val Val Pro Ser Glu Gly Leu Tyr
            20                  25                  30

Leu Ile Tyr Ser Gln Val Leu Phe Lys Gly Gln Gly Cys Pro Ser Thr
        35                  40                  45

His Val Leu Leu Thr His Thr Ile Ser Arg Ile Ala Val Ser Tyr Gln
    50                  55                  60

Thr Lys Val Asn Leu Leu Ser Ala Ile Lys Ser Pro Cys Gln Arg Glu
65                  70                  75                  80
```

<210> SEQ ID NO 4
<211> LENGTH: 80
<212> TYPE: PRT
<213> ORGANISM: Artificial sequence
<220> FEATURE:
<223> OTHER INFORMATION: Polypeptide

<400> SEQUENCE: 4

```
Gln Leu Gln Trp Leu Asn Arg Arg Ala Asn Ala Leu Leu Ala Asn Gly
1               5                   10                  15

Val Glu Leu Arg Asp Asn Gln Leu Val Val Pro Ser Glu Gly Leu Tyr
            20                  25                  30

Leu Ile Tyr Ser Gln Val Leu Phe Lys Gly Gln Gly Cys Pro Ser Thr
        35                  40                  45

His Val Leu Leu Thr His Thr Ile Ser Arg Ile Ala Val Phe His Gln
```

```
                50                  55                  60
Thr Lys Val Asn Leu Leu Ser Ala Ile Lys Ser Pro Cys Gln Arg Glu
 65                  70                  75                  80

<210> SEQ ID NO 5
<211> LENGTH: 10
<212> TYPE: PRT
<213> ORGANISM: Artificial sequence
<220> FEATURE:
<223> OTHER INFORMATION: Polypeptide

<400> SEQUENCE: 5

Arg Asp Asn Gln Leu Val Val Pro Ser Glu
 1               5                  10

<210> SEQ ID NO 6
<211> LENGTH: 10
<212> TYPE: PRT
<213> ORGANISM: Artificial sequence
<220> FEATURE:
<223> OTHER INFORMATION: Polypeptide

<400> SEQUENCE: 6

Asp Asn Gln Leu Val Val Pro Ser Glu Gly
 1               5                  10

<210> SEQ ID NO 7
<211> LENGTH: 10
<212> TYPE: PRT
<213> ORGANISM: Artificial sequence
<220> FEATURE:
<223> OTHER INFORMATION: Polypeptide

<400> SEQUENCE: 7

Asn Gln Leu Val Val Pro Ser Glu Gly Leu
 1               5                  10

<210> SEQ ID NO 8
<211> LENGTH: 10
<212> TYPE: PRT
<213> ORGANISM: Artificial sequence
<220> FEATURE:
<223> OTHER INFORMATION: Polypeptide

<400> SEQUENCE: 8

Gln Leu Val Val Pro Ser Glu Gly Leu Tyr
 1               5                  10

<210> SEQ ID NO 9
<211> LENGTH: 214
<212> TYPE: PRT
<213> ORGANISM: Homo sapiens

<400> SEQUENCE: 9

Asp Ile Gln Met Thr Gln Ser Pro Ala Ser Leu Ser Ala Ser Val Gly
 1               5                  10                  15

Glu Thr Val Thr Ile Thr Cys Arg Ala Ser Gly Asn Ile His Ile Tyr
                 20                  25                  30

Leu Ala Trp Tyr Gln Gln Lys Gln Gly Lys Ser Pro Gln Leu Leu Val
             35                  40                  45

Tyr Asn Ala Lys Thr Leu Ala Asp Gly Val Pro Ser Arg Phe Ser Gly
         50                  55                  60

Ser Gly Ser Gly Thr Gln Tyr Ser Leu Lys Ile Asn Ser Leu Gln Pro
 65                  70                  75                  80
```

```
Glu Asp Phe Gly Ser Tyr Tyr Cys Gln His Phe Trp Ser Ile Pro Trp
                85                  90                  95
Thr Phe Gly Gly Gly Thr Lys Leu Glu Ile Lys Arg Ala Asp Ala Ala
            100                 105                 110
Pro Thr Val Ser Ile Phe Pro Pro Ser Glu Gln Leu Thr Ser Gly
        115                 120                 125
Gly Ala Ser Val Val Cys Phe Leu Asn Asn Phe Tyr Pro Lys Asp Ile
    130                 135                 140
Asn Val Lys Trp Lys Ile Asp Gly Ser Glu Arg Gln Asn Gly Val Leu
145                 150                 155                 160
Asn Ser Trp Thr Asp Gln Asp Ser Lys Asp Ser Thr Tyr Ser Met Ser
                165                 170                 175
Ser Thr Leu Thr Leu Thr Lys Asp Glu Tyr Glu Arg His Asn Ser Tyr
            180                 185                 190
Thr Cys Glu Ala Thr His Lys Thr Ser Thr Ser Pro Ile Val Lys Ser
        195                 200                 205
Phe Asn Arg Asn Glu Cys
    210

<210> SEQ ID NO 10
<211> LENGTH: 454
<212> TYPE: PRT
<213> ORGANISM: Homo sapiens

<400> SEQUENCE: 10

Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr Asn Tyr
            20                  25                  30
Gly Met Asn Trp Val Lys Gln Ala Pro Gly Lys Gly Leu Lys Trp Met
        35                  40                  45
Gly Trp Ile Asn Thr Tyr Thr Gly Glu Pro Thr Tyr Ala Asp Asp Phe
    50                  55                  60
Lys Gly Arg Phe Ala Phe Ser Leu Glu Thr Ser Ala Asn Thr Ala Tyr
65                  70                  75                  80
Leu Gln Ile Asn Asn Leu Arg Asn Glu Gly Met Ala Thr Tyr Phe Cys
                85                  90                  95
Ala Arg His Tyr Arg Tyr Ala Trp Phe Pro Tyr Trp Gly Gln Gly Thr
            100                 105                 110
Leu Val Thr Val Ser Ala Ala Lys Thr Thr Pro Pro Ser Val Tyr Pro
        115                 120                 125
Leu Ala Pro Gly Cys Gly Asp Thr Thr Gly Ser Ser Val Thr Leu Gly
    130                 135                 140
Cys Leu Val Lys Gly Tyr Phe Pro Glu Ser Val Thr Val Thr Trp Asn
145                 150                 155                 160
Ser Gly Ser Leu Ser Ser Val His Thr Phe Pro Ala Leu Leu Gln
                165                 170                 175
Ser Gly Leu Tyr Thr Met Ser Ser Ser Val Thr Val Pro Ser Ser Thr
            180                 185                 190
Trp Pro Ser Gln Thr Val Thr Cys Ser Val Ala His Pro Ala Ser Ser
        195                 200                 205
Thr Thr Val Asp Lys Lys Leu Glu Pro Ser Gly Pro Ile Ser Thr Ile
    210                 215                 220
Asn Pro Cys Pro Pro Cys Lys Glu Cys His Lys Cys Pro Ala Pro Asn
```

```
            225                 230                 235                 240

Leu Glu Gly Gly Pro Ser Val Phe Ile Phe Pro Pro Asn Ile Lys Asp
                245                 250                 255

Val Leu Met Ile Ser Leu Thr Pro Lys Val Thr Cys Val Val Val Asp
                260                 265                 270

Val Ser Glu Asp Asp Pro Asp Val Gln Ile Ser Trp Phe Val Asn Asn
                275                 280                 285

Val Glu Val His Thr Ala Gln Thr Gln Thr His Arg Glu Asp Tyr Asn
                290                 295                 300

Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ser Pro Ile Glu Arg Thr Ile Ser Lys Ile Lys Gly Leu Val Arg Ala
                340                 345                 350

Pro Gln Val Tyr Ile Leu Pro Pro Ala Glu Gln Leu Ser Arg Lys
                355                 360                 365

Asp Val Ser Leu Thr Cys Leu Val Val Gly Phe Asn Pro Gly Asp Ile
                370                 375                 380

Ser Val Glu Trp Ala Ser Asn Gly His Thr Glu Glu Asn Tyr Lys Asp
385                 390                 395                 400

Thr Ala Pro Val Leu Asp Ser Asp Gly Ser Tyr Phe Ile Tyr Ser Lys
                405                 410                 415

Leu Asn Met Lys Thr Ser Lys Trp Glu Lys Thr Asp Ser Phe Ser Cys
                420                 425                 430

Asn Val Arg His Glu Gly Leu Lys Asn Tyr Tyr Leu Lys Lys Thr Ile
                435                 440                 445

Ser Arg Ser Pro Gly Lys
                450

<210> SEQ ID NO 11
<211> LENGTH: 7
<212> TYPE: PRT
<213> ORGANISM: Homo sapiens

<400> SEQUENCE: 11

Gln Leu Val Val Pro Ser Glu
1               5

<210> SEQ ID NO 12
<211> LENGTH: 10
<212> TYPE: PRT
<213> ORGANISM: Homo sapiens

<400> SEQUENCE: 12

Ala Leu Leu Ala Asn Gly Val Glu Leu Arg
1               5                   10

<210> SEQ ID NO 13
<211> LENGTH: 10
<212> TYPE: PRT
<213> ORGANISM: Homo sapiens

<400> SEQUENCE: 13

Leu Leu Ala Asn Gly Val Glu Leu Arg Asp
1               5                   10

<210> SEQ ID NO 14
```

```
<211> LENGTH: 10
<212> TYPE: PRT
<213> ORGANISM: Homo sapiens

<400> SEQUENCE: 14

Leu Ala Asn Gly Val Glu Leu Arg Asp Asn
1               5                   10

<210> SEQ ID NO 15
<211> LENGTH: 10
<212> TYPE: PRT
<213> ORGANISM: Homo sapiens

<400> SEQUENCE: 15

Ala Asn Gly Val Glu Leu Arg Asp Asn Gln
1               5                   10

<210> SEQ ID NO 16
<211> LENGTH: 10
<212> TYPE: PRT
<213> ORGANISM: Homo sapiens

<400> SEQUENCE: 16

Asn Gly Val Glu Leu Arg Asp Asn Gln Leu
1               5                   10

<210> SEQ ID NO 17
<211> LENGTH: 10
<212> TYPE: PRT
<213> ORGANISM: Homo sapiens

<400> SEQUENCE: 17

Gly Val Glu Leu Arg Asp Asn Gln Leu Val
1               5                   10

<210> SEQ ID NO 18
<211> LENGTH: 10
<212> TYPE: PRT
<213> ORGANISM: Homo sapiens

<400> SEQUENCE: 18

Val Glu Leu Arg Asp Asn Gln Leu Val Val
1               5                   10

<210> SEQ ID NO 19
<211> LENGTH: 10
<212> TYPE: PRT
<213> ORGANISM: Homo sapiens

<400> SEQUENCE: 19

Glu Leu Arg Asp Asn Gln Leu Val Val Pro
1               5                   10

<210> SEQ ID NO 20
<211> LENGTH: 10
<212> TYPE: PRT
<213> ORGANISM: Homo sapiens

<400> SEQUENCE: 20

Leu Arg Asp Asn Gln Leu Val Val Pro Ser
1               5                   10

<210> SEQ ID NO 21
<211> LENGTH: 10
<212> TYPE: PRT
```

<213> ORGANISM: Homo sapiens

<400> SEQUENCE: 21

Leu Val Val Pro Ser Glu Gly Leu Tyr Leu
1               5                   10

<210> SEQ ID NO 22
<211> LENGTH: 10
<212> TYPE: PRT
<213> ORGANISM: Homo sapiens

<400> SEQUENCE: 22

Val Val Pro Ser Glu Gly Leu Tyr Leu Ile
1               5                   10

<210> SEQ ID NO 23
<211> LENGTH: 10
<212> TYPE: PRT
<213> ORGANISM: Homo sapiens

<400> SEQUENCE: 23

Val Pro Ser Glu Gly Leu Tyr Leu Ile Tyr
1               5                   10

<210> SEQ ID NO 24
<211> LENGTH: 10
<212> TYPE: PRT
<213> ORGANISM: Homo sapiens

<400> SEQUENCE: 24

Pro Ser Glu Gly Leu Tyr Leu Ile Tyr Ser
1               5                   10

<210> SEQ ID NO 25
<211> LENGTH: 10
<212> TYPE: PRT
<213> ORGANISM: Homo sapiens

<400> SEQUENCE: 25

Ser Glu Gly Leu Tyr Leu Ile Tyr Ser Gln
1               5                   10

<210> SEQ ID NO 26
<211> LENGTH: 10
<212> TYPE: PRT
<213> ORGANISM: Homo sapiens

<400> SEQUENCE: 26

Glu Gly Leu Tyr Leu Ile Tyr Ser Gln Val
1               5                   10

<210> SEQ ID NO 27
<211> LENGTH: 10
<212> TYPE: PRT
<213> ORGANISM: Homo sapiens

<400> SEQUENCE: 27

Gly Leu Tyr Leu Ile Tyr Ser Gln Val Leu
1               5                   10

<210> SEQ ID NO 28
<211> LENGTH: 10
<212> TYPE: PRT
<213> ORGANISM: Homo sapiens

```
<400> SEQUENCE: 28

Leu Tyr Leu Ile Tyr Ser Gln Val Leu Phe
1               5                   10
```

PROTEIN FOR NEUTRALIZING PROGRAMMED NECROCYTOSIS PROMOTION ANTIBODY, AND APPLICATION OF PROTEIN

INCORPORATION BY REFERENCE OF THE SEQUENCE LISTING

The description incorporates by reference the Sequence Listing submitted herewith via EFS on Jan. 29, 2021. The Sequence Listing, identified as Sequence Listing.txt, is 14,836 bytes and was created on Jan. 29, 2021.

TECHNICAL FIELD

The present invention relates to the field of biomedicine; and in particular, the present invention relates to a protein capable of neutralizing cell necroptosis-promoting antibodies and its use in the treatment of inflammation.

BACKGROUND

Tumor necrosis factor α (TNF) is a multifunctional cytokine secreted by various cells, mainly macrophages and T cells. TNF exerts a variety of biological functions (1-3) through TNF receptors 1 and 2 (TNFR1 and TNFR2).

Many functions of TNF are mainly involved in three intracellular events: 1) stimulation of transcription factor nuclear factor kappa B (NF-κB), thereby leading to cell activation and cytokine production; 2) induction of external pathways of apoptosis; and 3) induction of necrosis. These active intracellular signaling pathways share some components but lead to different results: activation of NF-κB leads to the secretion of pro-inflammatory cytokines and cell survival as well as activation; apoptosis is a state of cell death characterized by activation of caspase-3, nuclear fragmentation, early presence of complete cell membrane, and little or no inflammatory response; however, necrosis is another mechanism of cell death in which there is no activation of caspase-3 and the integrity of the cell membrane is impaired. Necrosis leads to release of intracellular substances that stimulate strong immunity and inflammatory responses (4, 5). Under apoptosis, inhibition of caspase results in a programmed cell death that occurs with necrotic features and is called “necroptosis” (6-11). Since such necroptosis is an inflammatory process, it may be clinically associated with diseases such as rheumatoid arthritis, Crohn’s disease, and psoriasis. However, to date, factors that trigger necroptosis in these diseases have not yet been identified.

Fundamental changes in treating inflammatory diseases were obtained by directly targeting TNF molecules (monoclonal antibody) or using antagonists as false receptors to neutralize TNF (12), however completely blockage of functions of TNF may cause life-threatening side effects, such as, infections and tumors (13). TNF in many inflammatory diseases (e.g. rheumatoid arthritis, inflammatory bowel disease, psoriasis, etc.) have played an important role in pathology. It is very clinically effective to treat inflammatory diseases with anti-TNF. Anti-TNF biologics include anti-TNF monoclonal antibodies capable of neutralizing TNF, free TNF receptors, and the like. The market for anti-TNF formulations is $15 billion a year.

Despite these findings, the mechanism of cell and tissue destruction in inflammatory diseases remains unknown: induction of NF-κB is pro-survival and does not directly lead to cell death—in fact, it was found that NF-κB signaling blocks apoptosis in inflammatory bowel disease (14). It is believed that apoptosis suppresses inflammation (15). Necroptosis may be a possible mechanism of inflammation and cell/tissue destruction, but lacking evidence of clinical relevance in humans. For example, in non-viral inflammatory pathogenesis, it is not known which factor outside target cells triggers necroptosis (14, 16). Identification of these factors will clearly provide a biomarker for diagnosing and treating many inflammatory diseases.

In patients with sepsis, TNF is significantly elevated and is positively correlated with the severity of the disease. However, traditional TNF-blocking antibodies and free receptors are not effective in the treatment of sepsis, suggesting that other factors may play a key role in pathogenic process in synergism with TNF.

Therefore, there is an urgent need in the art for physical means to modulate, or even reverse cell necrosis, so that inflammatory diseases can be treated.

SUMMARY OF THE INVENTION

It is an object of the present invention to provide a technical means for modulating, or even reversing cellular necrosis, so that inflammatory diseases can be treated.

In a first aspect, a polypeptide that inhibits cell necrosis is provided in the present invention, and said polypeptide is derived from wild-type TNFα and comprises 10-200 amino acid residues and a sequence QLVVPSE (SEQ ID NO: 11), wherein said polypeptide does not bind to TNFR1 but competes with TNF for binding to a cell necrosis-promoting antibody.

In a specific embodiment, the wild-type TNFα is a human TNFα, the amino acid sequence of which is shown in SEQ ID NO: 1.

In a specific embodiment, the cell necrosis-promoting antibody has: a light chain shown in SEQ ID NO: 9; and/or a heavy chain shown in SEQ ID NO: 10.

In a specific embodiment, the amino acid sequence of the polypeptide is selected from a group consisting of: SEQ ID NOs: 2-8.

In a preferred embodiment, the polypeptide is a soluble polypeptide.

In a specific embodiment, the amino acid sequence of the polypeptide is shown in SEQ ID NO: 2, 3 or 4.

In a second aspect, a use of a polypeptide according to the first aspect of the invention for preparing a medicament for inhibiting cell necrosis or treating a cell necrosis-related disease is provided in the present invention.

In a specific embodiment, the cell necrosis-related disease is inflammatory disease.

In a specific embodiment, the inflammatory disease includes but is not limited to rheumatoid arthritis, Crohn’s disease, psoriasis, sepsis.

In a third aspect, a pharmaceutical composition for inhibiting cell necrosis is provided in the present invention, and said pharmaceutical composition comprises a therapeutically effective amount of the polypeptide according to the first aspect of the present invention and a pharmaceutically acceptable carrier.

In a preferred embodiment, the amino acid sequence of the polypeptide is selected from a group consisting of: SEQ ID NOs: 2-8.

In a preferred embodiment, the polypeptide is a soluble polypeptide.

In a preferred embodiment, the amino acid sequence of the polypeptide is shown in SEQ ID NO: 2, 3 or 4.

In a specific embodiment, the pharmaceutical composition is an intravenous injection.

In a fourth aspect, a dialysis device for treating a patient's blood is provided in the invention, and said dialysis device comprises a polypeptide according to the first aspect of the invention.

In a preferred embodiment, the dialysis device is used to remove or neutralize a cell necrosis-promoting antibody in the blood of the patient.

In a preferred embodiment, the cell necrosis-promoting antibody has: a light chain shown in SEQ ID NO: 9; and/or a heavy chain shown in SEQ ID NO: 10.

In a preferred embodiment, the dialysis device is a dialysis column.

In a fifth aspect, a method for inhibiting or neutralizing a cell necrosis-promoting antibody in the blood of a patient is provided in the present invention, comprising inhibiting or neutralizing the cell necrosis-promoting antibody in the blood of the patient using the polypeptide according to the first aspect of the present invention.

In a preferred embodiment, the cell necrosis-promoting antibody has: a light chain shown in SEQ ID NO: 9; and/or a heavy chain shown in SEQ ID NO: 10.

In a preferred embodiment, the method comprises administering the polypeptide of the first aspect of the invention, for example, by injection to a patient in need thereof for.

In a preferred embodiment, the method comprises inhibiting or neutralizing the cell necrosis-promoting antibody in the blood of the patient through dialysis using the polypeptide according to the first aspect of the invention.

In a preferred embodiment, the method comprises inhibiting or neutralizing the cell necrosis-promoting antibody in the blood of the patient by using a dialysis device comprising the polypeptide according to the first aspect of the invention.

In a preferred embodiment, the dialysis device is a dialysis column.

In a preferred embodiment, the method is for treating a cell necrosis-related disease.

In a preferred embodiment, the cell necrosis-related disease is inflammatory disease.

In a preferred embodiment, the inflammatory disease includes but is not limited to rheumatoid arthritis, Crohn's disease, psoriasis, sepsis.

It should be understood that, within the scope of the present invention, the above technical features of the present invention and the technical features specifically described in the following contents (such as embodiments) can be combined with each other to constitute a new or preferred technical solution, which is not necessary to repeat them one by one herein.

DESCRIPTION OF DRAWINGS

FIG. 11 shows the polypeptides of the present invention P12-10, P13-1, P13-2 and P13-3 are capable of competitively inhibiting binding of TNF to monoclonal antibody 244-12.

MODE FOR CARRYING OUT THE INVENTION

Figure 1:
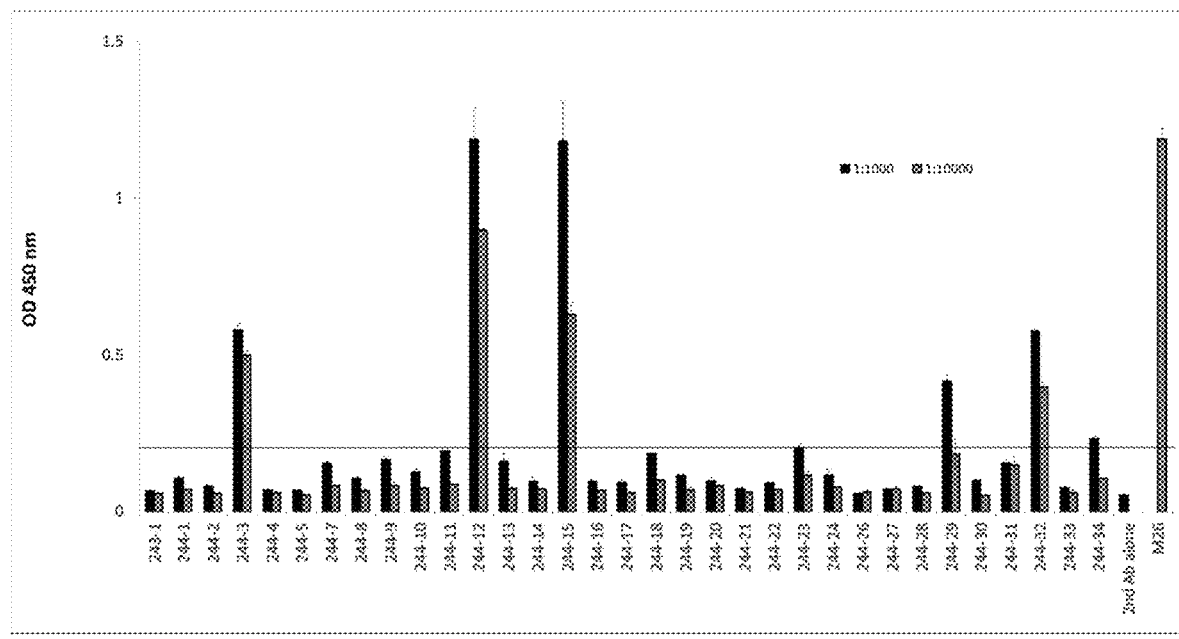
FIG. 1 shows the screening of a mAb that can bind to TNF from 33 mAbs, wherein ELISA test demonstrated that 244-12 binds TNF the strongest.

After extensive and intensive study, the inventors has unexpectedly found that, in the presence of TNF, autoantibody 244-12 can convert TNF-induced apoptosis into necroptosis, and then found that similar necroptosis-inducing autoantibodies are present in some patients with inflammatory diseases such as arthritis, sepsis, and the disease in these patients was aggravated. Moreover, the inventors prepared polypeptides capable of blocking the autoantibodies in the patients, which in turn can treat inflammation without causing serious side effects. Based on this, the present invention was completed.

Apoptosis or cell apoptosis as described herein refers to programmed death of a cell, i.e., death of cells through signal transduction. It is characterized by cell atrophy, cell nuclei rupture, but integrity of cell membrane can be maintained. Since the cell membrane is intact and apoptotic cells are quickly phagocytosed by macrophages, apoptosis does not cause inflammation.

The necrosis or cell necrosis described herein refers to the death of a cell that is destroyed by external forces and characterized by cell disruption and destruction and incompleteness of the cell membrane. In necrosis, the cells release many inflammatory substances such as nucleic acids, uric acid, HMGB1, and the like, thus causing inflammatory reactions.

The necroptosis or cell necroptosis described herein refers to the death of a cell through signal transduction. It is characterized by cell disruption and destruction and incompleteness of cell membrane. As the cell necrosis as mentioned above, during necroptosis, necrotic cells release many inflammatory substances such as nucleic acids, uric acid, HMGB1, and the like, thus causing inflammatory reactions.

TNF and Functions Thereof

TNF is a multifunctional cytokine secreted mainly by macrophages and T cells. It exerts a variety of biological functions through TNF receptor 1 and 2 (TNFR1 and TNFR2), including stimulation of transcription factor nuclear factor kappa B (NF-κB); induction of an external pathway of apoptosis; and induction of necrosis.

In most cases, stimulation to cells by TNF primarily activates NF-κB for cell survival. Apoptosis and necrosis are triggered only when NF-κB pathway is inhibited (24). It has been suggested that TNF stimulates membrane-bound complex I (25), which initiates NF-κB activation but does not initiate apoptosis/necrosis. However, if NF-κB activation is prevented, TNF stimulates its target cells to form a second complex (Complex II) in the cytoplasm that directs the signaling pathway to cell death.

All current studies emphasize the downstream consequences of TNF-TNFR1 binding. However, the delicate molecular basis has not been studied at the level of TNF-TNFR1 interactions that may lead to the observation of different cellular functions. Generally, the conventional concept is that TNF-TNFR1 binding is sufficient to initiate all TNF functions, including stimulating NF-κB and inducing cell death. The prior art also investigated short peptides derived from human TNF a, among which some significantly induce apoptosis, while some lead to cell necrosis. And the solubility of various short peptides may be significantly different, which will affect the drug performance of short peptides.

Antibody

As used herein, "antibody", "monoclonal antibody", "244-12" or "autoantibody" have the same meaning and refer to an antibody capable of binding TNF, in particular specifically binding sequence QLVVPSE (SEQ ID NO: 11), that is, the binding epitope is QLVVPSE (SEQ ID NO: 11). The antibody can cause necroptosis of cells.

In the context, the antibody include not only intact monoclonal antibody but also immunologically active antibody fragments such as Fab or (Fab')$_2$ fragments; antibody heavy chains; antibody light chains. In a specific embodiment, the antibody has: a light chain shown in SEQ ID NO: 9; and/or a heavy chain shown in SEQ ID NO: 10.

Polypeptide of the Invention

In order to provide a means for regulating or even reversing cell necrosis, a polypeptide is provided in the present invention which is capable of binding the aforementioned autoantibodies capable of causing necroptosis of cells without binding TNFR1, thereby inhibiting cell necrosis, which in turn can treat or reduce inflammation.

In a specific embodiment, a polypeptide is provided in the present invention, which is derived from wild-type TNF a and can inhibit cell necrosis, and said polypeptide comprises 10-200 amino acid residues (preferably 10-180, more preferably 10-160 amino acid residues) and sequence QLVVPSE (SEQ ID NO: 11). In a specific embodiment, the wild-type TNFα is human TNFα, the amino acid sequence of which is shown in SEQ ID NO: 1.

In a preferred embodiment, the amino acid sequence of the polypeptide is selected from a group consisting of: SEQ ID NOs: 2-8. In a further preferred embodiment, the polypeptide of the present invention is a soluble polypeptide so that it can provide excellent drug-producing properties.

In a specific embodiment, the amino acid sequence of the polypeptide is shown in SEQ ID NO: 2, 3 or 4.

Pharmaceutical Composition

Based on the polypeptide of the present invention, a pharmaceutical composition for inhibiting cell necrosis is further provided in the present invention, which comprises a therapeutically effective amount of the polypeptide of the present invention and a pharmaceutically acceptable carrier.

As used herein, the term "effective amount" or "therapeutically effective amount" refers to an amount which can exert function or activity to a human and/or animal and can be accepted by the human and/or animal.

As used herein, the "pharmaceutically acceptable" ingredient is a substance that is suitable for use in humans and/or mammals without undue adverse side effects (e.g., toxicity, irritation, and allergies), i.e., a substance having a reasonable benefit/risk ratio. The term "pharmaceutically acceptable carrier" refers to a carrier for the administration of a therapeutic agent, including various excipients and diluents.

The pharmaceutical composition of the present invention contains a safe and effective amount of the polypeptide of the present invention as an active ingredient and a pharmaceutically acceptable carrier. Such carriers include, but are not limited to, saline, buffer, dextrose, water, glycerol, ethanol, and a combination thereof. Usually, a pharmaceutical preparation should be matched with the administration method. The dosage form of the pharmaceutical composition of the present invention may be in a form of solid or solution, preferably in a form of solution, such as an injection, oral preparation (tablet, capsule, oral liquid), transdermal agent, sustained release agent. For example, it is prepared by a conventional method using physiological saline or an aqueous solution containing glucose and other adjuvants. The pharmaceutical composition is preferably prepared under aseptic conditions.

The effective amount of the active ingredient of the present invention may vary depending on the mode of administration and the severity of the disease to be treated. The selection of the preferred effective amount can be determined by a skilled person based on various factors (e.g., through clinical trials). Such factors include, but are not limited to: pharmacokinetic parameters of the active ingredient such as bioavailability, metabolism, half-life, etc.; severity of the disease of a patient to be treated, weight of a patient, immune status of a patient, administration route, and so on. Depending on the requirements on the treatment situation, several separate doses may be given daily or the dose may be proportionally reduced.

The pharmaceutically acceptable carriers, effective amounts of the active ingredients, and modes of administration described herein are well-known to a skilled person.

In view of the functions of the polypeptide and pharmaceutical composition of the present invention, a skilled person will know that they are capable of inhibiting cell necrosis, thereby treating cell necrosis-related diseases, including but not limited to inflammatory diseases. In a specific embodiment, the inflammatory disease includes but is not limited to rheumatoid arthritis, Crohn's disease, psoriasis, sepsis.

Based on the polypeptide and pharmaceutical composition of the present invention, a method for inhibiting cell necrosis or treating diseases associated with cell necrosis, such as inflammatory diseases is also provided in the present invention, comprising administering to a subject in need thereof a polypeptide of the present invention or a pharmaceutical composition comprising the polypeptide of the present invention.

Main Advantages of the Present Invention are:

1. In the present invention, a polypeptide capable of neutralizing autoantibodies that cause necroptosis of cells was found for the first time;
2. The results of the present invention have significant clinical significance;
3. The polypeptides of the present invention are capable of treating, alleviating or reducing the inflammatory response.
4. The polypeptide of the present invention does not bind to TNF receptor, therefore not affecting normal functions of TNF; unlike currently clinically used anti-TNF mAb or TNF free receptor in anti-inflammatory therapy, which will cause side effects, such as tuberculosis infections and tumors due to inhibiting of functions of TNF.

The present invention will be further described below with reference to specific embodiments. It should be understood that these examples are only for illustrating the present invention and are not intended to limit the scope of the present invention. The experimental methods with detailed conditions not specified in the following examples are generally performed under conventional conditions, such as those described in Sambrook et al., Molecular Cloning: A Laboratory Manual (New York: Cold Spring Harbor Laboratory Press, 1989), or according to conditions recommended by the manufacturer. Unless otherwise indicated, percentages and parts are by weight. The experimental materials used in the examples of the present invention can be obtained from commercially available sources unless otherwise specified.

Material and Method

Patient

Patients were recruited by a rheumatology clinic or ICU ward and all samples were stored at −80° C. until analysis. As a part of a therapeutic joint puncture, synovial fluid was drawn from the knee joint of an inflammatory disease patient. Rheumatoid arthritis was defined according to American College of Rheumatology 1987 or 2010 ACR/EULAR classification criteria; and other inflammatory joint diseases were diagnosed based on clinical criteria and X-ray photography. All patients with rheumatism respond positively to rheumatoid factor and have moderate disease activity. Patients with sepsis were diagnosed according to criteria established by American College of Chest Physicians in 1992. With the informed consent of the donor, samples and/or data are collected in accordance with national and institutional ethical requirements.

Cell Line, TNF and Polypeptide

Mouse fibrosarcoma L929 cells and human lymphocyte Jurkat A3 cells were purchased from American Type Culture Collection (ATCC, Manassas, Va.). Human C2812 chondrocytes were provided by Dr. Mary B. Goldring. SaOs-2 human osteoblast cells were purchased from Sigma. TNF was purchased from Immunotools (German).

Apoptosis and Necrosis Test

In the presence of TNF or TNF peptide with or without 20 µM z-VAD-FMK (R & D Systems, Minneapolis, Minn.) or 20 µM Necrotatin-1 (PeproTech, Rocky Hill, N.J.) (Immunotools, Friesoythe, Germany), cells were incubated overnight (or the time shown in the incubation diagram). In some experiments, TNF was co-cultured with cells and the monoclonal antibody with indicated concentration or synovial fluid. Cells were stained using live/dead cell staining kit (Invitrogen, Paisley, UK) according to the manufacturer's manual and fixed using a cytofix/cytoperm fixation/permeabilization solution kit (BD Pharmingen, Oxford, UK). Intracellular staining was then performed using FITC-conjugated anti-caspase-3 antibody (Cell Signaling Technology, Danvers, Mass., USA). Cells were harvested by CyAn flow cytometer (Beckman Coulter, Fullerton, Calif.), and data were analysed by Flowjo (Tree Star Inc. Ashland, Oreg.).

ELISA

Screening Monoclonal Antibody/Inhibition Test

ELISA plates were coated with 2 µg/ml of TNF at 4° C. overnight, or at 37° C. for 2 hours, and then incubated with a monoclonal antibodies at 37° C. for 1 hour. A second antibody conjugated to HRP was used to detect the reaction. For the inhibition assay, TNFR1 or synovial fluid was added together with the monoclonal antibody.

TNF Binding to TNFR1

The binding of TNFR1 to TNF was tested by ELISA as follows: ELISA plates were coated at 4° C. overnight with 1.5 µg/ml of TNF or mTNF-HA, or at 37° C. for 2 hours. After incubation at 37° C. with TNFR1 (1 µg/ml) for 2 hours, the plates were incubated with anti-TNFR1 or anti-HA antibody for another two hours, second anti-mouse IgG antibody conjugated with HRP was added for 30 minutes, and then its substrate was added for testing. Colors were developed and detected at OD 450 nm using Wallace Victor2 1420 multi-label counter (PerkinElmer, Mass., Massachusetts, USA).

L929 Cell Immunofluorescence Microscopy

At room temperature, 20 ng/ml of TNF and 2 µg/ml of mAb M26 or 244-12 were incubated for 1 hour. The mixture of TNF/M26 or TNF/244-12 were incubated on ice with L929 cells grown on coverslip for an another 15 minutes. The cells were fixed with 4% paraformaldehyde (PBS formulation) were for 10 minutes, blocked with phosphate buffer containing 0.5% BSA and 0.1% cold water fish gelatin for 15 minutes, and then incubated with rabbit anti-TNFR1 antibody (Abcam) for 1 hour. The cells were washed with PBS and then incubated with the relevant secondary antibody coupled to Alexa Fluor 488 or Alexa Fluor 568 (Invitrogen). Then the sample washed with PBS was mounted with Gelvatol/DABCO (Sigma-Aldrich). DNA was counterstained with DAPI (Sigma-Aldrich). All samples were analyzed by fluorescence microscopy at 60× using Nikon Eclipse 80i. Images were taken with NIS-Elements AR3.0 software using Hamamatsu camera.

Synthesis and Detection Method for Polypeptide and Protein:

Using a conventional method, corresponding coding nucleotide sequences for the amino acid sequences shown in SEQ ID NO: 2-4 were synthesized, and then the polypeptides were expressed and purified using *E. coli*. The purified product was confirmed by SDS electrophoresis and a spectrometer (Bruker Daltonics Ultraflex TOF/TOF mass spectrometer).

The amino acid sequences shown in SEQ ID NO: 5-8 and modified sequences thereof, such as N-terminal or C-terminal biotinylaed (if needed) was synthesized according to Fmoc strategy on an automated polypeptide synthesizer APEX396. The synthesized polypeptide was confirmed with a spectrometer (Bruker Daltonics Ultraflex TOF/TOF mass spectrometer).

EXAMPLE

Example 1. Preparation of Monoclonal Antibody 244-12 and Identification of Binding Epitope Thereof 33 monoclonal antibodies by conventional methods were prepared and the bindings of the prepared monoclonal antibodies to TNF were tested by the inventors, wherein the monoclonal antibody 244-12 was proved to be the strongest one binding to TNF by ELISA test.

Afterwards, the binding epitope of monoclonal antibody 244-12 was identified as QLVVPSE (SEQ ID NO: 11) by the inventors.

Example 2. Conversion of TNF-related Apoptosis to Necroptosis by Monoclonal Antibody 244-12

The inventors studied the effects of monoclonal antibody (mAb) 244-12 on TNF function.

Figure 2:
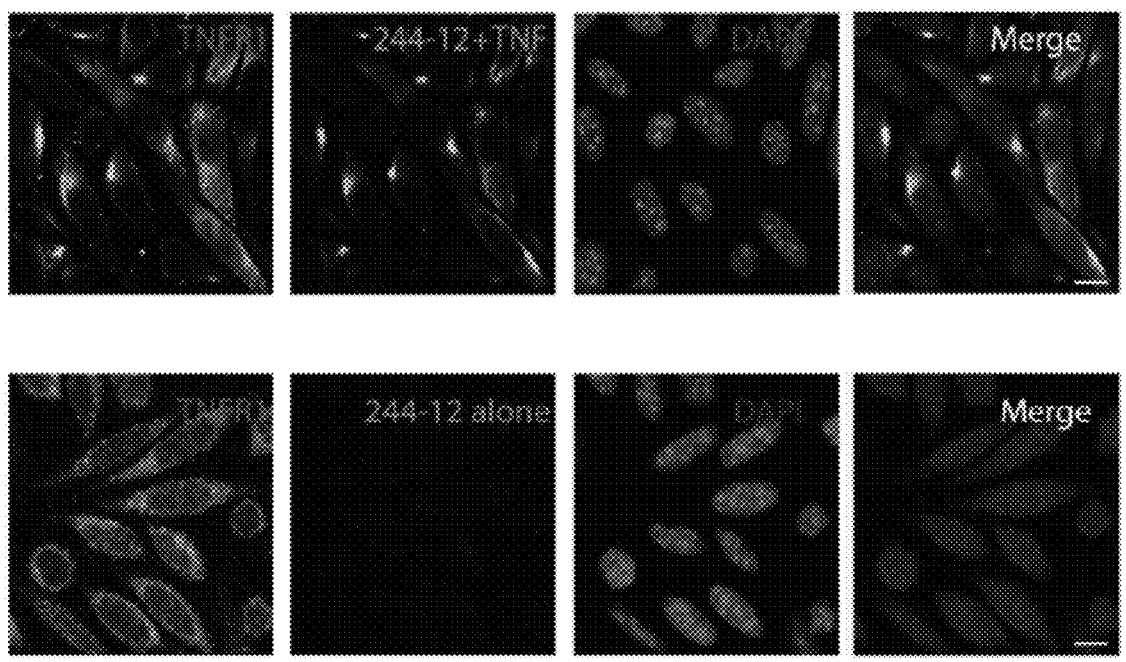
FIG. 2 shows that the binding of antibody 244-12 to TNF does not affect the binding of TNF to cell surface receptors, where "Merge" indicates combination, "alone" indicates that there is antibody 244-12 alone.

Firstly, the confocal micrograph in FIG. 2 shows that binding of monoclonal antibody 244-12 to TNF did not affect binding of TNF to TNF receptors. Under a confocal microscope, TNF receptors were stained as red and 244-12 was stained as green. The above panel shows that when TNF was present, green and red overlap (yellow), indicating 244-12 overlapping with TNF and TNF receptors; the lower panel shows that in the absence of TNF, there was only red, indicating that 244-12 cannot directly bind to cell surface.

Figure 3:
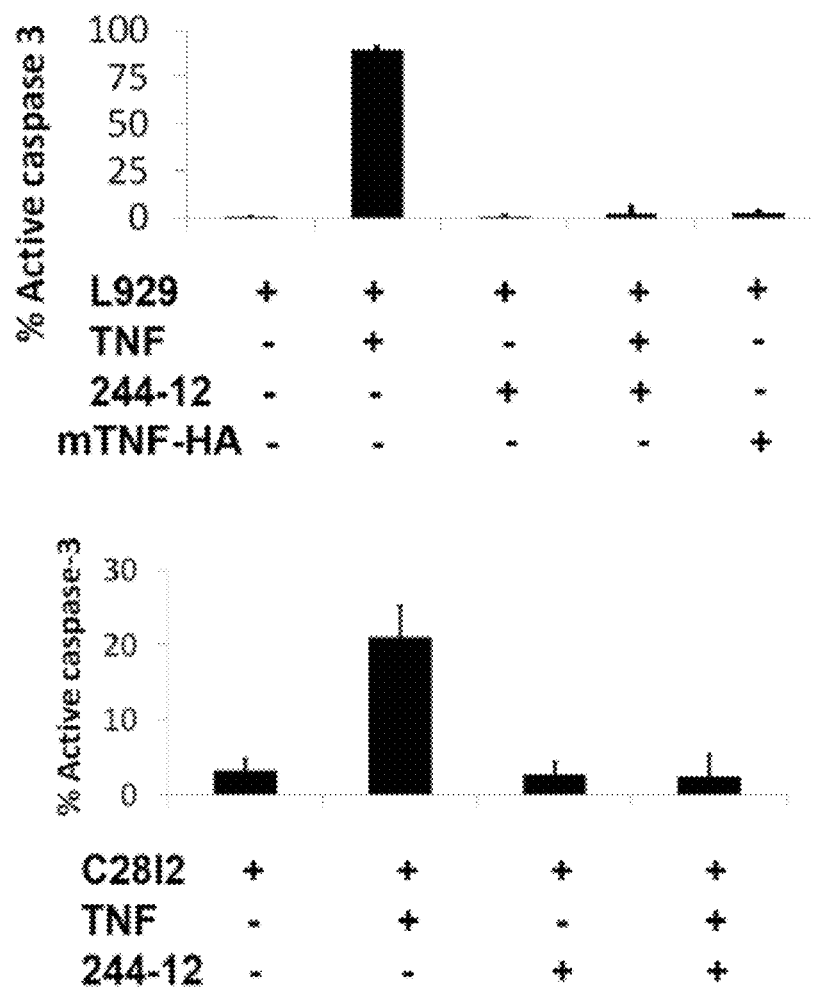
FIG. 3 shows that antibody 244-12 blocks TNF-induced cell apoptosis (i.e., active caspase-3 expression) in both cell lines. Among them, the above panel is L929 cells (mouse fibroblastoma cells); and the lower panel is C2812 cells (chondrocytes)

Subsequently, the inventors observed that stimulation of TNF to L929 cells caused apoptosis (expression of active caspase-3), however, when mAb 244-12 was added, apoptosis is inhibited (inhibition of active caspase-3). FIG. 3 shows that monoclonal antibody 244-12 blocked TNF-induced apoptosis (i.e., expression of Active caspase-3) in two cell lines, L929 cells (mouse fibroblastic cells, upper panel) and C2812 cells (chondrocytes, lower panel).

Figure 4:
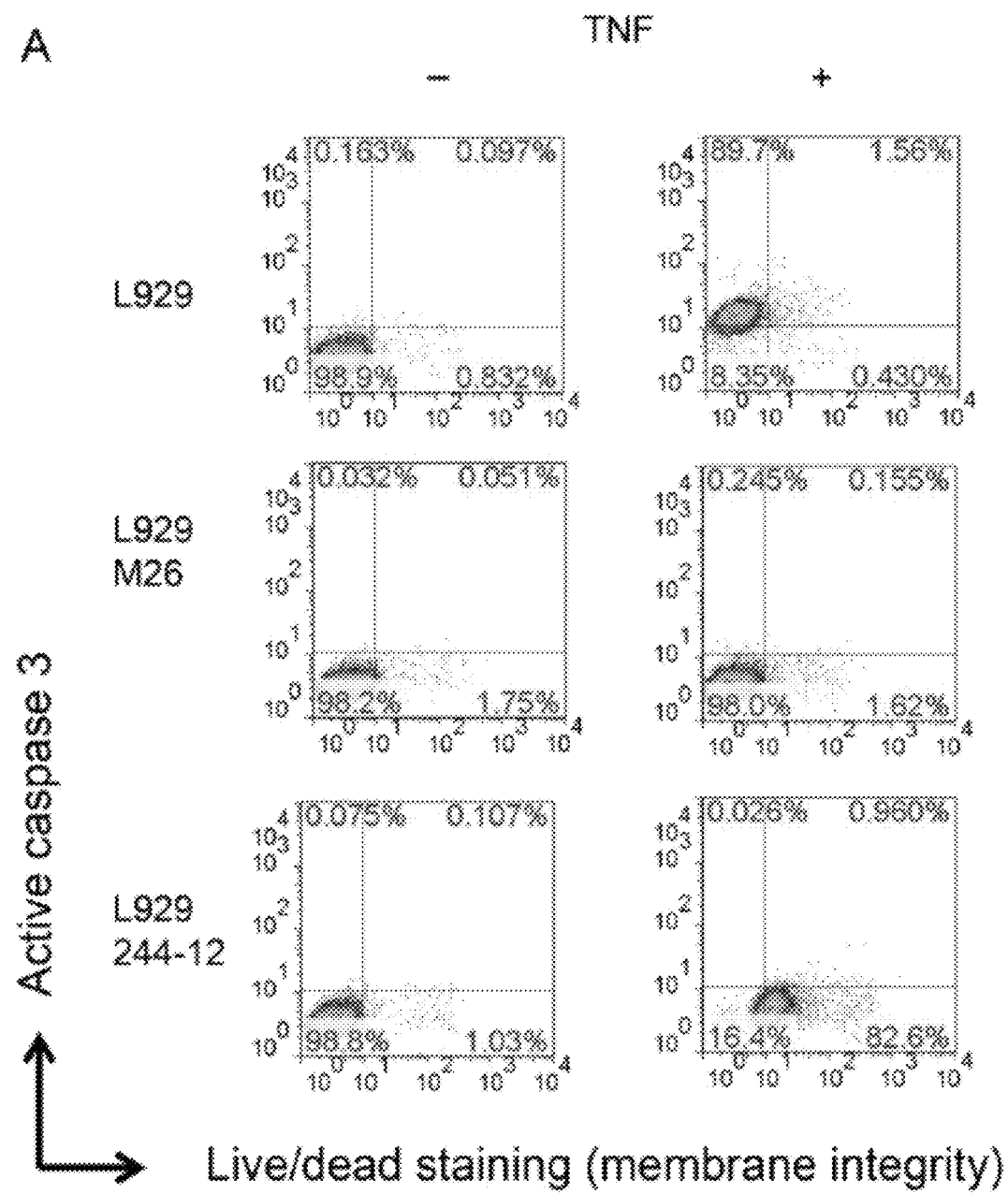
FIG. 4 shows that antibody 244-12 and TNF cause L929 cell necrosis. In the figure, the Y-axis indicates apoptosis (active caspase-3); and the abscissa indicates cell necrosis (disruption of cell membrane integrity). Among them, TNF caused cell apoptosis (the right of upper panel); L929 cells survived (the right of middle panel) by adding control antibody M26 (blocking binding of TNF to a receptor); and L929 cell necrosis (the right of bottom panel) by adding 244-12 and TNF.

However, it is unexpected to find that, when the monoclonal antibody 244-12 was added to TNF and L929 cells, apoptosis was inhibited but necrosis occurred in the cells. FIG. 4 shows that antibody 244-12 and TNF caused necrosis of L929 cell. TNF caused apoptosis (the right of upper panel); addition of control antibody M26 (blocking TNF binding to receptors) caused survival of L929 cells (the right of middle panel); and addition of 244-12 and TNF caused necrosis of L929 cells (the right of bottom panel).

Figure 5:
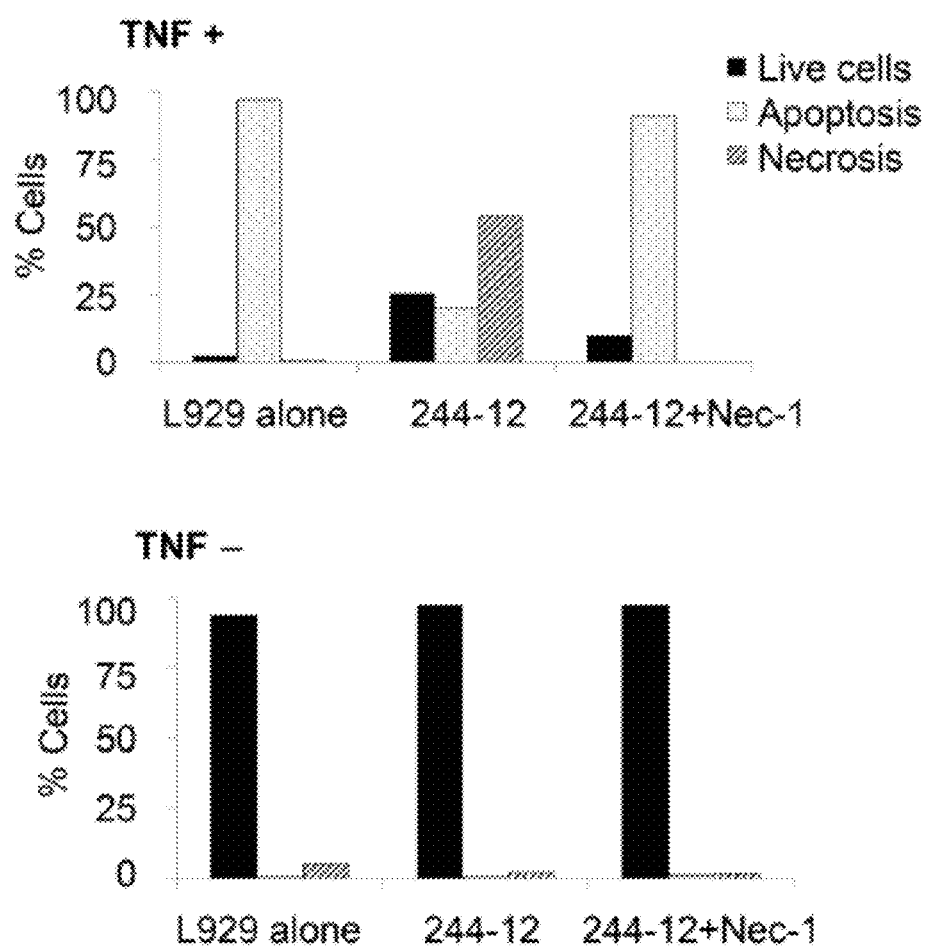
FIG. 5 shows that necrosis caused by antibody 244-12+TNF can be inhibited by Nec-1, wherein, for 244-12+TNF, after Nec-1 was added (the right of above panel), the cell necrosis was converted into apoptosis, which shows that cell necrosis is through signaling, that is, necroptosis.

The inventors have further demonstrated that the necrosis caused by 244-12+TNF was via signal transduction. FIG. 5 shows that the necrosis induced by the antibody 244-12 of the present invention+TNF can be inhibited by Nec-1. After "244-12+TNF" was added to Nec-1, cell necrosis was converted into apoptosis (the right of above panel), indicating that cell necrosis was via signal transduction, that is, necroptosis.

Figure 6:
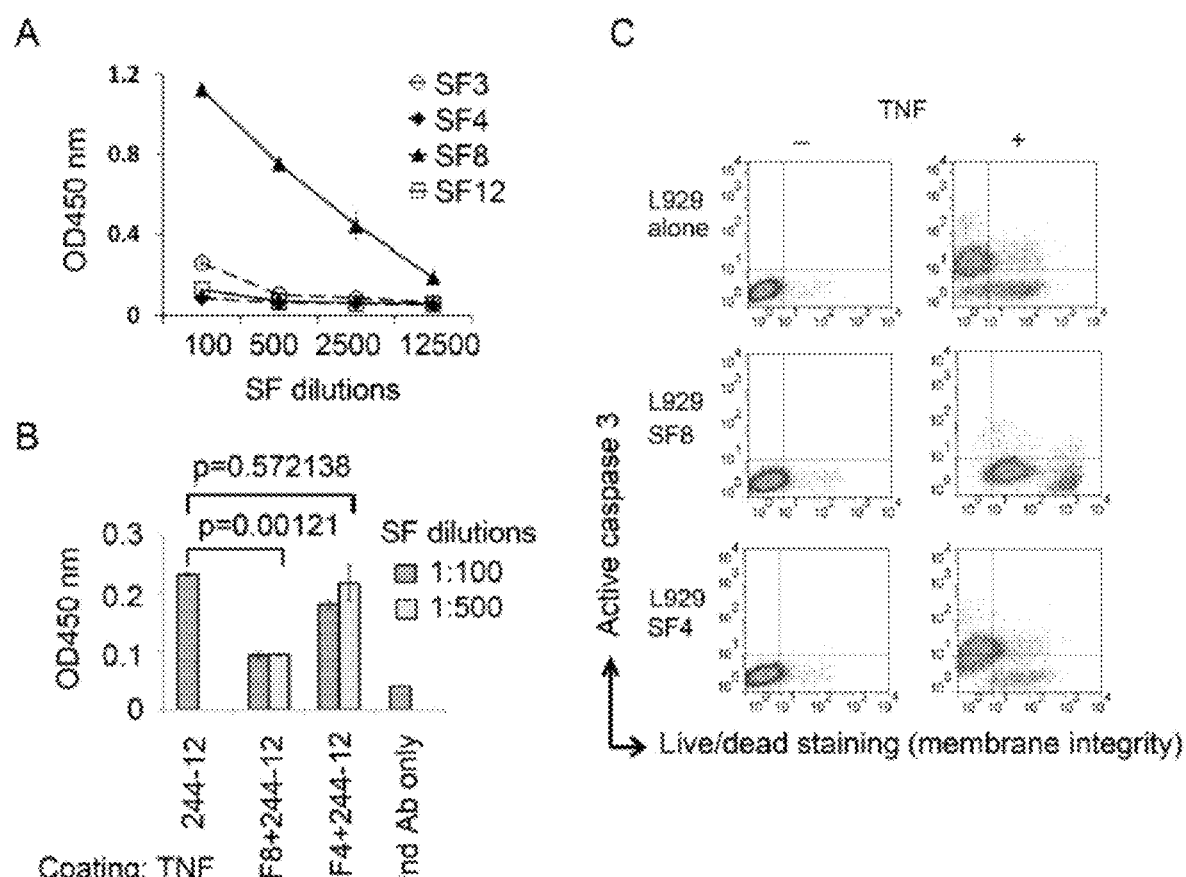
FIG. 6 shows that autoantibodies in synovial fluid of a patient with rheumatoid arthritis trigger necroptosis.

Example 3. Autoantibody in Synovial Fluid of Rheumatoid Arthritis Triggers Necroptosis We have unexpectedly found that high level of antibodies was present in joint fluid of patients with untreated rheumatoid arthritis or osteoarthritis (FIG. 6A). These antibodies can compete with 244-12 for antigen binding sites (FIG. 6B). These antibody-containing joint fluids can cause cell necroptosis (FIG. 6C).

FIG. 6A shows that anti-TNF auto-antibodies were present in joint fluid of some arthritis patients. Very high level of autoantibodies was present in the joint fluid of patient SF8. 6B shows that autoantibodies competed with 244-12 for TNF binding sites. When SF8 joint fluid was added to 244-12 and TNF binding assay (ELISA), the binding of 244-12 to TNF was inhibited. 6C shows that SF8 joint fluid caused necroptosis in the presence of TNF. TNF induced apoptosis in L929 cells (the right of above panel). When SF8 joint fluid is added, the cells converted into necroptosis (the right of middle panel). While the control joint fluid SF4 did not cause necrosis (the right of below panel).

Figure 7:
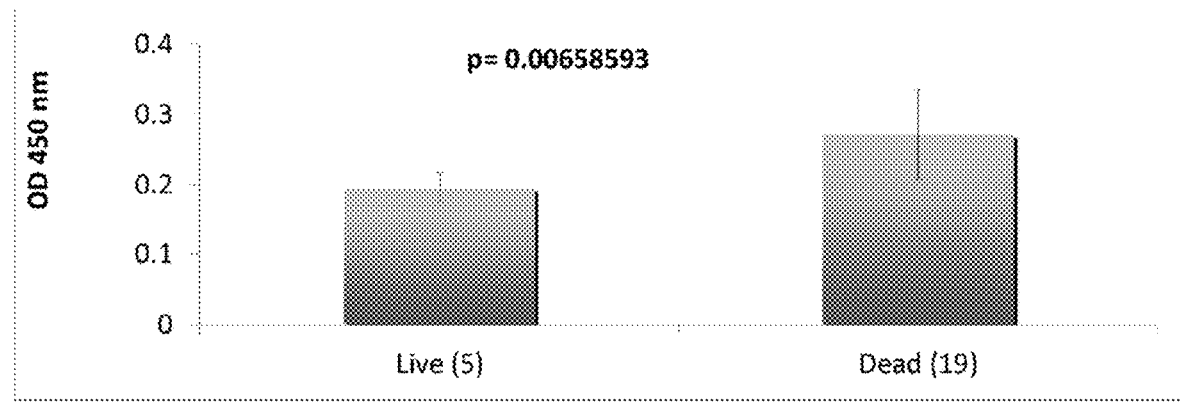
FIG. 7 shows the average level of an antibody competing with the antibody 244-12 of the present invention for antigen-binding site in recovered sepsis patients (5) and the died patients (19). The difference between the two groups is very significant. $P<0.01$.
Figure 8:
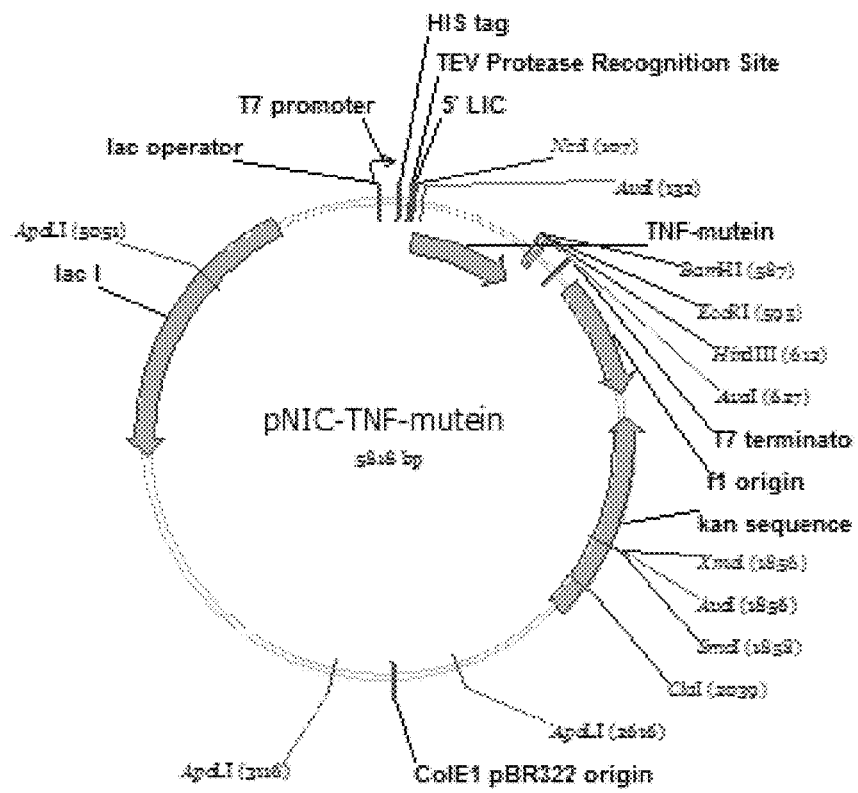
FIG. 8 is a schematic representation of pNIC28Bsa4 vector, wherein important components related to clone expression are shown.

The inventors further observed 24 patients with sepsis. In 14 patients, antibodies competing with 244-12 for antigen binding site were detected and in the other 10 patients, similar antibodies were not contained. All of the 14 patients containing such antibodies competing with 244-12 for antigen binding site, despite intensive care and treatment, still died. While for the other 10 patients, 5 patients died, and other 5 patients have been healed after 2-3 weeks. The antibody levels in the dead patients were significantly higher than those in the recovered group (p<0.01) (FIG. 7).

Example 4

The inventors further studied antibodies that specifically bind to other TNF molecules and fragments thereof, and did not find that these antibodies have the effects of converting TNF-related apoptosis into necroptosis.

In addition, the present inventors performed screening with full-length TNF and found that only antibodies specifically binding to QLVVPSE (SEQ ID NO: 11) have the effects of converting TNF-related apoptosis into necroptosis.

Example 5. Preparation of Polypeptides of the Invention

The following polypeptides of the present invention were prepared, tested and confirmed according to "Synthesis and detection method for Polypeptide and protein" in "Materials and Methods":

```
SEQ ID NO: 2:
VRSS SRTPSDKPVA HVVANPQAEG QLQWLNRRAN

ALLANGVELR DNQLVVPSEG LYLIYSQVLF KGQGCPSTHV

LLTHTISRIA VFHQTKVNLL SAIKSPCQRE TPEGAEAKPW

YEPIYLGGVF QLEKGDRLSA EINRPDYLDF AESGQVYFGI

IAL;

P11-17:
                                    (SEQ ID NO: 3)
QLQWLNRRAN ALLANGVELR DNQLVVPSEG LYLIYSQVLF

KGQGCPSTHV LLTHTISRIA VSYQTKVNLL SAIKSPCQRE;

P11-17 (mutant, SY mutation):
                                    (SEQ ID NO: 4)
QLQWLNRRAN ALLANGVELR DNQLVVPSEG LYLIYSQVLF

KGQGCPSTHV LLTHTISRIA VFHQTKVNLL SAIKSPCQRE;
```

-continued

P12-10:
(SEQ ID NO: 5)
RDNQLVVPSE;

P13-1:
(SEQ ID NO: 6)
DNQLVVPSEG;

P13-2:
(SEQ ID NO: 7)
NQLVVPSEGL;

P13-3:
(SEQ ID NO: 8)
QLVVPSEGLY.

Example 6. Activity of the Polypeptide of the Present Invention to Neutralize Cell Necrosis-Promoting Antibodies The present inventors have further studied the ability of the polypeptide of the present invention to bind cell necrosis-promoting antibodies, thereby competitively inhibiting the binding of TNF with cell necrosis-promoting antibodies and the ability of the polypeptide of the present invention to inhibit cell necrosis.

Figure 9:
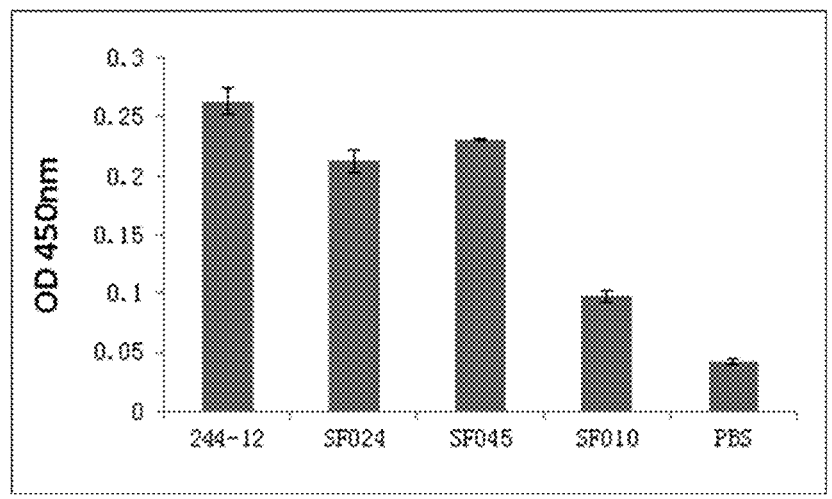
FIG. 9 shows that the polypeptide P11-17 of the present invention can not only bind to the purified cell necrosis-promoting antibody (244-12), but also bind to autoantibodies (SF024, SF045) in synovial fluid of an arthritis patient with cell necrosis-promoting antibody. However, the response to the synovial fluid was negative in a control patient without a cell necrosis-promoting antibody (SF010). The plate was coated with 2 μg/ml of P11-17, blocked with BSA and incubated with 244-12, SF024, SF045 and SF010 for 1 hour at room temperature, and then identified anti-mouse or human IgG secondary antibodies labeled with horseradish peroxide dismutase.

As shown in FIG. 9, the polypeptide P11-17 (SEQ ID NO: 3) of the present invention can bind to purified cell necrosis-promoting antibody (244-12), but also bind to cell necrosis-promoting antibodies present in joint fluid of arthritis patients (Sample SF024, sample SF045). However, the reaction with synovial fluid of a control patient without autoantibodies (SF010) was negative. ELISA plates were coated with 2 µg/ml of P11-17, blocked with BSA, incubated with 244-12, SF024, SF045, SF010 at room temperature for 1 hour, and then identified with horseradish peroxidase dismutase-labeled anti-mouse or human IgG secondary antibody.

Figure 10:
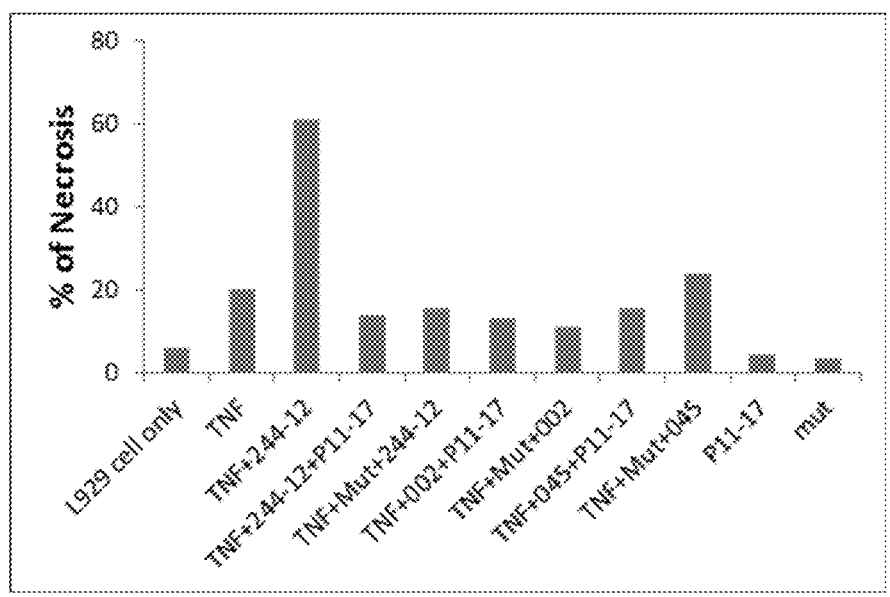
FIG. 10 shows that the polypeptides of the present invention, P11-17 and the polypeptide of SEQ ID NO: 2 can effectively inhibit cell necrosis, whether cell necrosis is caused by a purified cell necrosis-promoting antibody (244-12) or by a cell necrosis-promoting (SF002, SF045) in a patient's synovial fluid.

FIG. 10 shows that both the polypeptide P11-17 and SEQ ID NO: 2 of the present invention can effectively inhibit cell necrosis, whether cell necrosis was caused by purified cell necrosis-promoting antibody (244-12) or by cell necrosis-promoting antibody in the synovial fluid of patients (SF002, SF045).

FIG. 11 shows that polypeptides P12-10, P13-1, P13-2 and P13-3 of the present invention are capable of competitively inhibiting the binding of TNF to monoclonal antibody 244-12. P12-10, P13-1, P13-2 and P13-3 significantly inhibited the binding of TNF to mAb 244-12. METHODS: plates were coated with TNF, and the indicated peptides were added to each well, and then the monoclonal antibody 244-12 was added. If the polypeptide can bind to 244-12, the binding of 244-12 to TNF can be inhibited.

The ability of the polypeptides of the invention to bind to cell necrosis-promoting antibodies and the ability of the polypeptides of the invention to inhibit cell necrosis are summarized in the following table.

| | Apoptosis | Necrosis | Stimulation of cell proliferation | binding to cell necrosis-promoting antibodies | Inhibition of cell necrosis |
|---|---|---|---|---|---|
| TNFα | Yes | Yes | Yes | Yes | no |
| P12-10 | no | no | no | Yes | Yes |
| P13-1 | no | no | no | Yes | Yes |
| P13-2 | no | no | no | Yes | Yes |
| P13-3 | no | no | no | Yes | Yes |
| P11-17 | no | no | no | Yes | Yes |
| P11-17 mutation | no | no | no | Yes | Yes |
| Free TNF mutations | no | no | no | Yes | Yes |

Discussion

Based on the findings of the present invention, the present inventors proposed new therapeutic strategies for inflammation. The mechanism of necroptosis involves autoantibodies and TNF. Necroptosis is one of the causes for inflammation. Currently, one treatment strategy for inflammatory diseases is to block TNF by inhibiting TNF. This strategy is effective in suppressing inflammation, but may lead to life-threatening side effects, such as TB or lymphoma. The inventors proposed an alternative method of blocking autoantibodies by the polypeptide of the present invention (without binding to TNFR1). The results of this strategy may be reduction of inflammatory burden and inhibition of necroptosis, and maintain TNF in situ, thereby preventing tumors and serious infections, such as TB.

All references mentioned in this application are incorporated by reference in this application, as if each were incorporated by reference individually. In addition, it should be understood that after reading the above teachings of the present invention, those skilled in the art can make various changes or modifications to the present invention, and these equivalent forms also fall within the scope defined by the appended claims of the present application.

REFERENCES

1. Chan, K F, Siegel, M R, and Lenardo, J M 2000. Signaling by the TNF receptor superfamily and T cell homeostasis. Immunity 13:419-422.
2. Thoma, B., Grell, M., Pfizenmaier, K., and Scheurich, P. 1990. Identification of a 60-kD tumor necrosis factor (TNF) receptor as the major signal transducing component in TNF responses. J Exp Med 172: 1019-1023.
3. Idriss, H T, and Naismith, J H 2000. TNF a and the TNF receptor superfamily: structure-function relationship(s). Microsc Res Tech 50: 184-195
4. Van Herreweghe, F., Festjens, N., Declercq, W., and Vandenabeele, P. 2010. Tumor necrosis factor-mediated cell death: to break or to burst, that's the question. Cell Mol Life Sci 67:1567-1579.
5. Kono, H., and Rock, K L 2008. How dying cells alert the immune system to danger. Nat Rev Immunol 8:279-289.
6. Declercq, W., Vanden Berghe, T., and Vandenabeele, P. 2009. RIP kinases at the crossroads of cell death and survival. Cell 138:229-232.
7. Hitomi, J., Christofferson, D E, Ng, A., Yao, J., Degterev, A., Xavier, R J, and Yuan, J. 2008. Identification of a molecular signaling network that regulates a cellular necrotic cell death Pathway. Cell 135: 1311-1323.
8. Galluzzi, L., and Kroemer, G. 2008. Necroptosis: a specialized pathway of programmed necrosis. Cell 135: 1161-1163.

9. Vandenabeele, P., Galluzzi, L., Vanden Berghe, T., and Kroemer, G. 2010. Molecular mechanisms of necroptosis: an ordered cellular explosion. Nature Reviews Molecular Cell Biology 11:700-714.
10. Berghe, TV, Vanlangenakker, N., Parthoens, E., Deckers, W., Devos, M., Festjens, N., Guerin, C J, Brunk, U T, Declercq, W., and Vandenabeele, P. 2010 Necroptosis, necrosis and secondary necrosis on similar cellular disintegration features. Cell Death Differ 17:922-930.
11. Chan, F K, Shisler, J., Bixby, J G, Felices, M., Zheng, L., Appel, M., Orenstein, J., Moss, B., and Lenardo, M J 2003. A role for tumor Necrosis factor receptor-2 and receptor-interacting protein in programmed necrosis and antiviral responses. J Biol Chem 278:51613-51621.
12. Feldmann, M. 2009. Translating molecular insights in autoimmunity into effective therapy. Annu Rev Immunol 27:1-27.
13. Scheinfeld, N. 2004. A comprehensive review and evaluation of the side effects of the tumor necrosis factor α blockers etanercept, infliximab and adalimumab. J Dermatolog Treat 15:280-294.
14. Gunther, C., Neumann, H., Neurath, M F, and Becker, C. 2013. Apoptosis, necrosis and necroptosis: cell death regulation in the intestinal epithelium. Gut 62:1062-1071.
15. Rock, K L, and Kono, H. 2008. The inflammatory response to cell death. Annu Rev Pathol 3:99-126.
16. Linkermann, A., and Green, D R 2014. Necroptosis. N Engl J Med 370:455-465.

The invention claimed is:

1. An isolated polypeptide that inhibits cell necrosis, wherein the amino acid sequence of the polypeptide is selected from the group consisting of SEQ ID NOs: 2-5.

2. The polypeptide of claim 1, wherein said polypeptide does not bind to TNFRI but competes with TNF for binding to a cell necrosis-promoting antibody and the cell necrosis-promoting antibody comprises a light chain shown in SEQ ID NO: 9 and a heavy chain shown in SEQ ID NO: 10.

3. The polypeptide of claim 1, wherein the polypeptide is a soluble polypeptide.

4. A pharmaceutical composition for inhibiting cell necrosis, comprising a therapeutically effective amount of the polypeptide of claim 1.

5. The pharmaceutical composition of claim 4, wherein the pharmaceutical composition is a composition for an intravenous injection.

6. A dialysis device for treating a patient's blood, wherein said dialysis device comprises the